(12) United States Patent
Macaulay

(10) Patent No.: US 6,362,146 B1
(45) Date of Patent: *Mar. 26, 2002

(54) PERSONAL WASHING COMPOSITIONS

(75) Inventor: Ernest Weatherley Macaulay, Bebington (GB)

(73) Assignee: Unilever Home & Personal Care USA, division of Conopco, Inc., Greenwich, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/326,519

(22) Filed: Jun. 4, 1999

(30) Foreign Application Priority Data

Jun. 5, 1998 (GB) ............................... 9812181

(51) Int. Cl.$^7$ ................................. A61K 7/50
(52) U.S. Cl. ....................... 510/159; 510/438; 510/441; 424/59; 424/70.9
(58) Field of Search ................ 424/451, 452, 424/455, 59, 70.9, 642; 510/159, 438, 441

(56) References Cited

U.S. PATENT DOCUMENTS

| 3,580,853 A | | 5/1971 | Parran, Jr. ................ 510/382 |
| 3,753,916 A | | 8/1973 | Parran, Jr. ................ 510/382 |
| 4,129,645 A | * | 12/1978 | Barnett et al. ............. 424/60 |
| 4,897,308 A | * | 1/1990 | Vanlerbeghe et al. ..... 428/402.2 |
| 5,063,057 A | * | 11/1991 | Spellman et al. ........... 424/401 |
| 5,223,250 A | | 6/1993 | Mitchell et al. ............. 424/59 |
| 5,425,939 A | * | 6/1995 | Guerro et al. ........... 424/78.02 |
| 5,476,660 A | | 12/1995 | Somasundaran ............ 424/401 |
| 5,500,223 A | * | 3/1996 | Behan et al. ............... 424/451 |
| 5,556,617 A | * | 9/1996 | Ribier et al. ............. 424/78.02 |
| 5,716,920 A | * | 2/1998 | Glenn, Jr. et al. .......... 510/159 |
| 6,043,204 A | * | 3/2000 | Kaufman et al. ........... 510/130 |
| 6,066,608 A | * | 5/2000 | Glenn, Jr. ................... 510/159 |

FOREIGN PATENT DOCUMENTS

| EP | 0386898 | 9/1990 |
| EP | 0573229 | 12/1993 |
| WO | 95/22311 | 8/1995 |
| WO | 95/28912 | 11/1995 |
| WO | 96/02229 | 2/1996 |
| WO | 96/02230 | 2/1996 |

OTHER PUBLICATIONS

Trade Literature on "Sun Caps" from SunSmart.
International Search Report Application No. PCT/EP 99/0310 mailed Sep. 28, 1999.

* cited by examiner

Primary Examiner—Cynthia H Kelly
Assistant Examiner—Dawn Garrett
(74) Attorney, Agent, or Firm—Roland A. Koatz

(57) ABSTRACT

A personal washing composition containing
  a) surfactant selected from anionic, nonionic, zwitterionic and cationic surfactants, soaps and mixes thereof;
  b) polymeric deposition aid;
  c) encapsulated sunscreen.

7 Claims, No Drawings

PERSONAL WASHING COMPOSITIONS

The present invention relates to personal washing compositions.

Increased awareness of the problems associated with exposure to UV radiation in sunlight has led to the much greater use of sunscreens.

Commercially available organic sunscreen products typically contain from about 3 to about 26% of one or more UV absorbing chemicals. These products are applied to the surface of the skin as a thin film, typically 10–15 µm, and the chemicals act as a filter to diminish the penetration of the harmful UV radiation to the cells of the epidermis. These sunscreens are typically applied in the form of a cream, oil, lotion, alcohol or gel carrier. However, the US Food and Drug Administration has only approved a limited number of such chemicals as "safe and effective" agents in protecting skin against UV radiation, and is now limiting the amount of such agents in compositions for topical administration.

Physical or inorganic sunscreens, on the other hand, comprise particles of a relatively physiologically inert sunblock, i.e. UV-absorbing, compound typically suspended in a cream or lotion. Materials frequently utilized for this purpose include kaolin, talc, titanium dioxide and zinc oxide. These physical sunscreens are typically messy and occlusive. Moreover they form a visible, opaque or coloured layer on the surface of the skin which may be cosmetically unacceptable. These products may also promote undesirable skin complaints.

In addition, such commercially available sunscreen products are only usually applied when the user thinks that they will be at risk from prolonged exposure to the sun. However, incidental exposure to the sun of skin which is not normally covered by clothing is also deleterious, and very few people bother to apply sunscreen to account for this.

Therefore, it is desirable to provide means of applying sunscreens to the skin or hair on a regular basis, to protect the skin from the deleterious effects of UV irradiation during casual exposure to sunlight without the need for separate application. The incorporation of sunscreens into personal washing compositions has been suggested. However, personal washing compositions are designed to remove any particulate or oily soil adhering to the skin or hair and, therefore, it is difficult to deliver oily or particulate materials, particularly sunscreens to the skin or hair from personal washing compositions.

Detergent compositions, for example shampoos, comprising an anionic surfactant, water-insoluble particles and a cationic polymer have been described in U.S. Pat. No. 3,580,853 (Parran), with the aim of depositing the particles onto the hair. In the detergent compositions described in that patent the cationic polymers are water-soluble cationic nitrogen containing polymers that have a molecular weight within the range from 2,000 to 3,000,000 and have a cationic charge density greater than 0.001 in aqueous solution. The "cationic charge density" of a polymer refers to the ratio of the number of positive charges on a monomeric unit of which the polymer is comprised to the molecular weight of said monomeric unit. The cationic charge density multiplied by the polymer molecular weight determines the number of positively charged active sites of a given polymer chain.

Although this patent gives an example of a toilet soap bar containing an organic sunscreen, a benzophenone based compound, the amount of deposition of the sunscreen onto the skin is not revealed.

EP-A-386 898 describes a shampoo composition which contains sunscreen materials. In order to increase their deposition onto the hair, a cationic polymer is added, and the preferred polymer is a cationic derivative of a polygalactomannan gum.

We have now found that the use of an encapsulated sunscreen provides better deposition than the use of solid or liquid sunscreens. Further, surprisingly, we have found that the higher proportion of encapsulating material to sunscreen, while maintaining the amount of sunscreen in the final product constant, greatly enhances the proportion of sunscreen deposited.

Thus, according to a first aspect of the present invention, there is provided a personal washing composition containing
a) surface active agent selected from anionic, nonionic, zwitterionic and cationic surfactants, soaps and mixes thereof;
b) polymeric deposition aid;
c) encapsulated sunscreen.

In further aspects this invention provides a process for washing human skin, using such a composition, and the use of such a composition for cleaning skin whilst depositing sunscreen on the skin.

Features of the invention, including various optional and preferred possibilities will now be discussed in more detail.

In personal washing compositions of the invention, the surface active agent can be selected from any known surfactant suitable for topical application to the human body. Mild surfactants, i.e. surfactants which do not damage the stratum corneum, the outer layer of skin, are particularly preferred.

One preferred anionic surfactant is fatty acyl isethionate of formula:

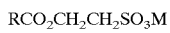

where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Another preferred anionic surfactant is alkyl ethoxy sulphate of formula:

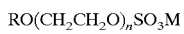

where R is an alkyl group of 8 to 22 carbon atoms, n ranges from 0.5 to 10 especially 1.5 to 8, and M is a solubilising cation as before.

Other possible anionic surfactants include alkyl glyceryl ether sulphates, sulphosuccinates, taurates, ethoxylated taurates, sarcosinates, sulphoacetates, alkyl phosphate, alkyl phosphate esters and acyl lactylate, alkyl glutamates, alkyl glycinates, alkyl sulphates, alkyl succinates, N-alkoyl sarcosinates, alkyl ether carboyxlates, alpha-olefin sulphonates, mono and di-alkyl phosphates, especially their sodium, magnesium, ammonium, and mono-, di, and tri-ethanolamine salts, and mixtures thereof.

Sulphosuccinates may be monoalkyl sulphosuccinates having the formula: $R^5O_2CCH_2CH(SO_3M)CO_2M$; and amido-MEA sulphosuccinates of the formula: $RCONCH_2CH_2O_2CCH_2CH(SO_3M)CO_2M$; wherein $R^5$ ranges from $C_8$–$C_{20}$ alkyl, preferably $C_{12}$–$C_{15}$ alkyl and M is a solubilising cation.

Sarcosinates are generally indicated by the formula: $R_5CON(CH_3)CH_2CO_2M$, wherein R ranges from $C_8$–$C_{20}$ alkyl, preferably $C_{12}$–$C_{15}$ alkyl and M is a solubilising cation.

Taurates are generally identified by the formula: $R^5CONR^6CH_2CH_2SO_3M$, wherein $R^5$ ranges from $C_8$–$C_{20}$ alkyl, preferably $C_{12}$–$C_{15}$ alkyl, $R^6$ ranges from $C_1$–$C_4$ alkyl, and M is a solubilising cation.

If the surface active agent comprises soap, the soap is preferably derived from materials with a $C_8$ to $C_{22}$ saturated and/or unsaturated carbon chain and, preferably, is a potassium soap with a $C_{12}$ to $C_{18}$ carbon chain.

Mixtures of any of the foregoing surface active agents may also be used.

It is also preferable that the composition includes at least one cosurfactant agent with skin-mildness benefits. Suitable materials are zwitterionic detergents which have an alkyl or alkenyl group of 7 to 18 carbon atoms and comply with an overall structural formula

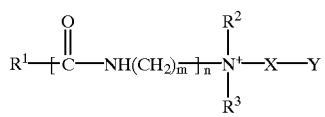

where $R^1$ is alkyl or alkenyl of 7 to 18 carbon atoms; $R^2$ and $R^3$ are each independently alkyl, hydroxyalkyl or carboxyalkyl of 1 to 3 carbon atoms; m is 2 to 4; n is 0 or 1; X is alkylene of 1 to 3 carbon atoms optionally substituted with hydroxyl; and Y is —$CO_2$ or —$SO_3$.

Zwitterionic detergents within the above general formula include simple betaines of formula:

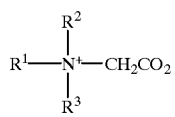

and amido betaines of formula:

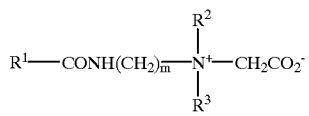

where m is 2 or 3.

In both formulae R, R and R are as defined previously. $R^1$ may, in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is a sulphobetaine of formula:

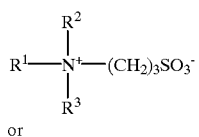

or

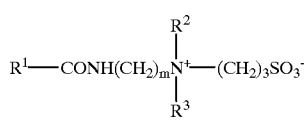

where
m is 2 or 3, or variants of these in which —$(CH_2)_3SO_3^-$ is replaced by:

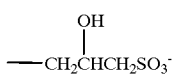

$R^1$, $R^2$ and $R^3$ in these formulae are as defined previously.

Other useful co-surfactants include alkyl amine oxides, alkanolamides and amphoacetates.

A composition of this invention may contain nonionic surfactant, suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol.

Another useful class of nonionics are the block co-polymers of ethylene oxide and propylene oxide. Glycoside surfactants are typically of the general formula:

in which G is a residue of a pentose or hexose, R'O is an alkoxy group, x is at least unity and R is an organic hydrophobic group from 6 to 20 carbon atoms which is preferably aliphatic, either saturated or unsaturated, notably straight or branched alkyl, alkenyl, hydroxyalkyl or hydroxyalkenyl. Particularly, R may be alkyl or alkenyl of 7 to 14 or 16 carbon atoms.

The value of t in the general formulae above is preferably zero, so that the —(R'O)$_t$— unit of the general formulae is absent. In that case the general formulae become:

If t is non-zero, it is preferred that R'O is an ethylene oxide residue. Other possibilities are propylene oxide and glycerol residues. If the parameter t is non-zero so that R'O is present, the value of t (which may be an average value) will preferably lie in the range from 0.5 to 10.

The group G is typically derived from fructose, glucose, mannose, galactose, talose, gulose, allose, altrose, idose, arabinose, xylose, lyxose and/or ribose. Preferably, the G is provided substantially exclusively by glucose units. Intersaccharide bonds may be from a 1-position to a 2, 3, 4 or 6-position of the adjoining saccharide. Hydroxyl groups on sugar residues may be substituted, e.g. etherified with short alkyl chains of 1 to 4 carbon atoms. Preferably a sugar residue bears no more than one such substituent.

The value x, which is an average, is usually termed the degree of polymerization. Desirably x varies between 1 and 8. Values of x may lie between 1 and 3, especially 1 and 1.8.

Alkyl polyglycosides of formula RO(G)$_x$, i.e. a formula as given above in which t is zero, are available from Horizon Chemical company, BASF and Henkel. O-alkanoyl glucosides of formula $RCO_2$–(G)x are described in International Patent Application WO 88/10147 (Novo Industri A/S). In particular the surfactants described therein are glucose esters with the acyl group attached in the 3- or 6-position such as 3-O-acyl-D-glucose or 6-O-acyl-D-glucose. Notable are 6-O-alkanoyl glucosides, in which the alkanoyl group incorporates an alkyl or alkenyl group having from 7 to 13 carbon atoms.

The glucose residue may be alkylated in its 1-position with an alkyl group having from 1 to 4 carbon atoms, such as ethyl or isopropyl. Alkylation in the 1-position enables such compounds to be prepared by regiospecific enzymatic synthesis as described by Bjorkling et al. (J. Chem. Soc., Chem. Commun. 1989 p934).

Aldobionamides are amides of an aldobionic acid or aldobionolactone. Aldobionic acids are disaccharides or polysaccharides in which the aldehyde group (generally found at the $C_1$ position of the sugar) has been replaced by a carboxylic acid. Upon drying they cyclise to aldobionolactones. The disaccharide may in particular be lactose or maltose, so that the aldobionamide is a lactobionamide or maltobionamide. Further information about aldobionamides and their preparation is given in EP-A-550278.

Descriptions of alkyl polyhydroxy fatty acid amides are found in U.S. Pat. No. 2,965,576, EP 220676, EP 550557 and documents referred to therein.

The surface active agent is preferably present in total amount of from 2 to 40% by weight, and preferably from 5 or 8 up to 30% by weight based on the whole composition. The amount of anionic surfactant is preferably from 2 or 4 up to 30 or 40% by weight of the composition. If a zwitterionic as the cosurfactant is present, the amount is preferably 0.5 to 15% by weight of the composition.

The polymeric deposition aids of the compositions of the present invention are preferably polymers which carry a cationic charge. The preferred polymers are cationic derivatives of guar gum, and more particularly a polygalactomannan gum. The gum occurs naturally as guar gum, the principal component of the seed of the guar plant, *Cyamopsis tetragonalobus*.

The guar molecule is essentially a straight chain mannan branched at quite regular intervals with single membraned galactose units on alternate mannose units. The mannose units are linked to each other by means of beta (1–4) glycosidic linkages. The galactose branching is accomplished through an alpha (1–6) linkage. The cationic derivatives are obtained by reactions between the hydroxyl groups of the polygalactomannan and reactive quaternary ammonium compounds. The degree of substitution with the cationic groups is desirably at least 0.01 and preferably at least 0.05, for example from 0.08 to 0.5.

Suitable cationic guar gum derivatives are those given the CTFA designation guar hydroxypropyl trimonium chloride, available commercially for example as JAGUAR™ C13S, which has a low degree of substitution of the cationic groups, about 0.13, and a high viscosity. The low degree of cationic substitution leads to a cationic charge density of 0.0008. The "cationic charge density" of a polymer as that term is used in U.S. Pat. No. 3,580,853 (Parran) refers to the ratio of the number of positive charges on a monomeric unit of which the polymer is comprised to the molecular weight of said monomeric unit. The cationic charge density multiplied by the polymer molecular weight determines the number of positively charged active sites of a given polymer chain.

Other suitable materials include that known as JAGUAR C15, having a moderate degree of substitution and a low viscosity, JAGUAR C17, (high degree of substitution, 0.25–0.31, hence cationic charge density of 0.0016, high viscosity) and JAGUAR C16 which is a hydroxypropylated cationic guar derivative containing a low level of substituent groups as well as cationic quaternary ammonium groups. The degree of substitution of the cationic groups is 0.11–0.16, and the average number of moles of substitution of hydroxypropyl groups is 0.8–1.1. JAGUAR C16 has a cationic charge density of 0.0008. Also suitable is JAGUAR 162 which is a high transparency, medium viscosity guar having a low degree of substitution.

Other suitable deposition aids include quaternary nitrogen substituted cellulose ether derivatives such as those commercially available as the Polymer JR series.

The polymeric deposition aid is preferably present in the washing composition in an amount of from 0.1 to 3% based on the weight of the whole composition.

Suitable encapsulated sunscreens have been described in WO 95/28912, and are available in emulsion form under the Trade Mark "Suncaps", from SunSmart Inc, Wainscott, N.Y., USA, but these are not the only suitable examples. Each capsule consists of an organic sunscreen active or combination of organic sunscreen active, trapped within a matrix. The matrix is typically a wax or oil—but may also be a polymeric material. The wax may be natural or synthetic, and may be mixes of alkyl wax esters, resins, and other vegetable matter components; clay-treated microcrystalline waxes; oxidised hydrocarbon waxes; natural and synthetic beeswax, auto-oxidised beeswax, candelilia, carnauba, and synthetic waxes prepared by esterification of natural plant-derived fatty acids and alcohols; various grades of paraffin waxes; and natural and synthetic oils. These capsules are supplied as an emulsion in a carrier. This may be aqueous. However, depending on the nature of the sunscreen active, particularly its relative solubility in the surfactant phase, the carrier can also be an oil. Suitable oils include mineral oil, thickened mineral oil, triglyceride oils, petrolatum, silicone oils, silicone waxes, and silicone-hydrocarbon co-polymers.

It is preferred that the encapsulated sunscreen is present in the composition in an amount such that the amount of sunscreen active in the composition is between 0.5 and 15 wt %. The lower limit may be as high as 1 or 2 wt %, and the upper limit may be only 12 or 10 wt %.

The sunscreen active may usually provide from 5 to 60% of the encapsulated sunscreen capsule, and more preferably from 5 or 8% up to 40 or 50%. A range from 5 to 40% may be most preferred, but the upper limit of this range may be lower, such as 20 or even 15 wt %.

Therefore, if the amount of sunscreen active in the sunscreen emulsion is low, the emulsion may provide a substantial proportion of the total formulation.

A personal washing composition according to the invention may also include minor amounts of other optional ingredients such as antibacterial agents, foam boosters, pearlescers, perfumes, dyes, colouring agents, preservatives, thickeners, proteins, other polymers, phosphate esters and buffering agents. The personal washing composition may also include moisturising agents including triglycerides, petrolatum, other cosmetic oils, humectants such as glycerol and skin emollients such as silicone oils.

The invention will now be further described by way of example only with reference to the following examples.

EXAMPLE 1 AND COMPARATIVE EXAMPLES

Personal washing compositions in the form of opacified liquids, containing synthetic detergent active, were prepared with the following general composition:

| Synthetic detergent-based composition | |
|---|---|
| Ingredient | wt. % |
| Sodium Laureth Sulphate | 13.00 |
| Cocoamido Propyl Betaine | 2.00 |
| Phenoxyethanol | 0.78 |
| Preservatives | 0.37 |
| Modified Polystyrene Latex | 0.44 |
| Perfume | 1.11 |

-continued

| Synthetic detergent-based composition | |
|---|---|
| Ingredient | wt. % |
| Sodium Chloride | 0.90 |
| JAGUAR C-13-S | 0.0 or 0.70 |
| Sunscreen active (encapsulated or not) | 2, 5 or 10 |
| Water | balance to 100 |

Some of the compositions prepared contained JAGUAR C-13-S as deposition aid, whilst others did not. The sunscreen active used was Octyl Methoxycinnamate (OMC) and was provided either in encapsulated form or not. If not encapsulated, the OMC was added neat to give the amount of active required (2, 5 or 10 wt % of the total composition). If the sunscreen active was encapsulated, the capsules used were Suncaps™ 664, available from SunSmart Inc., supplied as an emulsion which has a composition as follows:

| Ingredients | wt. % |
|---|---|
| Octyl Methoxycinnamate | 21.7 |
| Waxes | 25.4 |
| Water | 52.9 |

Thus the sunscreen active comprises 46.1 wt % of the encapsulated sunscreen capsules' non-aqueous contents, which constitute 47.1 wt % of the emulsion. The waxes used in the product are: C18-38 hydroxy stearyl stearate; PEG Carnauba; Dimethicone Copolyol beeswax; PVP/Eicosene Copolymer; Sorbitan Tristearate; Steareth-100; and PEG-100 Stearate. The emulsion, if used, was added in sufficient quantity to provide the sunscreen active in an amount of 2, 5 or 10 wt % of the total composition.

The Suncaps™ 664 emulsion is added to the washing composition at $\leq 40°$ C. to avoid damaging the capsules.

The amount of deposition of sunscreen active was measured as follows. Whole pigskin is obtained from a local abattoir where it is removed from the pig immediately after slaughter and is not subjected to any treatment. The skin is washed with water after removal and is cut into manageable portions (approximately 30 cm square), placed in self sealing polythene bags and stored in a domestic freezer until needed.

When needed the pigskin is removed from the freezer and allowed to defrost before any hair is removed using a pair of hair clippers. The pigskin is then cut into suitable samples (approximately 12 cm×15 cm) and stretched onto an expanded polystyrene support, where it is held in place with dissecting pins.

The pigskin is wetted with approximately 100 ml water (at 30° C.). 1.0 gram of washing composition containing encapsulate is applied to the wet surface and the surface is washed using a to and fro motion for 30 seconds. The skin is then rinsed by pouring 3×100 ml water (at 30° C.) over the surface. The surface is patted dry with paper towel and allowed to dry in air for at least 2 minutes before extraction.

The extraction is carried out by placing a glass cylinder 3.5 cm in diameter on the treated surface of the pigskin and holding it in position such that there is sufficient contact to form a seal between the cylinder rim and the skin. 3 ml absolute ethanol is introduced to the cylinder and allowed to contact the skin for ~2 minutes before being removed and transferred to a glass vial. The process is repeated twice with the aliquots of alcohol being combined in the glass vial. The volume of alcohol in the vial is then made up to 10 ml. Three independent sites are extracted on each piece of pigskin and three separate pieces of pigskin are subjected to each treatment yielding a total of nine measurements for each treatment.

The concentration of sunscreen active in each extract is determined by measuring the UV absorbance at a wavelength corresponding to the maximum absorbance peak in the UV spectrum of the sunscreen being examined using an Hitachi U-2000 UV/visible spectrophotometer (in the case of Octyl Methoxycinnamate maximum absorption occurs at ~310 nm) and comparing this with a set of calibration standards of known concentration. If the absorption of the extract is outside the linear response range determined from the standards the extract is serial dilutions are made until its absorbance falls within the linear range. The area of extraction and the volume of ethanol used to extract each site are chosen such that the concentration in ppm of sunscreen active determined by absorbance corresponds to deposition on the surface in $\mu g/cm^2$.

The 9 measurements for each composition were averaged and the results obtained (including standard error of the mean), are set out in the table below:

| | | Amount of sunscreen active deposited ($\mu g/cm^2$) | | |
|---|---|---|---|---|
| | Was | | | |
| Deposition Polymer present | sunscreen active encapsulated | 2% sunscreen active | 5% sunscreen active | 10% sunscreen active |
| * No | No | 6.2 ± 0.4 | 12.5 ± 1.2 | 24.8 ± 1.7 |
| * No | Yes | 5.9 ± 0.3 | 10.0 ± 1.3 | 17.2 ± 1.2 |
| * Yes | No | 7.9 ± 0.5 | 17.3 ± 0.7 | 31.8 ± 5.8 |
| Yes | Yes | 10.4 ± 1.0 | 20.4 ± 1.4 | 39.6 ± 4.1 |

* Comparative Examples

When the sunscreen active is encapsulated and deposition aid is present, the amount of active deposited is greater than the amount deposited either when the sunscreen active is not encapsulated or when no polymer deposition aid is present.

EXAMPLE 2

Two different formulations were prepared. The first was a synthetic detergent-based washing composition as in Example 1, but always containing the polymeric deposition aid JAGUAR C-13-S present at level of 0.70 wt. %. The second was a soap based washing composition made from fatty acids neutralised with potassium hydroxide, as follows:

| Soap-based Composition | |
|---|---|
| Ingredients | wt. % |
| Lauric acid | 8.63 |
| Myristic Acid | 8.63 |
| Potassium Hydroxide | 11.88 |
| Stearic Acid | 10.76 |
| Ethylene Glycol Monostearate | 6.00 |
| PEG 6000 Distearate | 2.00 |
| Preservative | 0.05 |
| Propan-1, 2-diol | 5.00 |
| Glycerol | 13.00 |
| Ethylene diamine tetraacetic acid | 0.25 |

-continued

Soap-based Composition

| Ingredients | wt. % |
| --- | --- |
| Perfume | 0.40 |
| Imidazolidinyl urea | 0.20 |
| Jaguar C-13-S | 0.70 |
| Sunscreen capsules emulsion sufficient to provide 2% sunscreen active | from 9 to 36 |
| Water | to 100 |

Sunscreen encapsulate emulsion was included in both these formulations in an amount which resulted in a constant 2% concentration of sunscreen active (OMC) in the final product. The three emulsions of encapsulates used were:

| Suncaps ™ Formulation number | Overall Composition of the emulsion | | | % wt of sunscreen active in capsules |
| --- | --- | --- | --- | --- |
| | Sunscreen active (wt. %) | Waxes etc (wt. %) | Water (wt. %) | |
| 664 | 21.7 | 25.4 | 52.9 | 46.1 |
| 1051 | 11.1 | 36.2 | 52.7 | 23.5 |
| 1053 | 5.6 | 41.8 | 52.6 | 11.8 |

The deposition of sunscreen was determined as in Example 1, and the results obtained are shown in the table below:

| Suncaps ™ formulation | 664 | 1051 | 1053 |
| --- | --- | --- | --- |
| % wt of sunscreen active in capsules | 46.1 | 23.5 | 11.8 |
| Amount of Suncaps emulsion in composition (%) | 9.2 | 18.0 | 35.7 |
| Amount of active deposited ($\mu$g/cm$^2$) from soap based compositions | 4.4 | 4.5 | 6.1 |
| Amount of active deposited ($\mu$g/cm$^2$) from synthetic based compositions | 3.8 | 4.7 | 5.6 |

This table shows the surprising result that increasing the amount of encapsulating material relative to the sunscreen active, while keeping the amount of sunscreen active in the final product constant, improves the deposition of the sunscreen active onto the skin.

EXAMPLE 3 AND COMPARATIVE EXAMPLES

Personal washing compositions with the same detergent mixture as in Example 1 were prepared with the following general composition:

| Ingredient | wt. % |
| --- | --- |
| Sodium Laureth Sulphate | 13.00 |
| Cocoamido Propyl Betaine | 2.00 |
| Phenoxyethanol | 0.78 |
| Preservatives | 0.37 |
| Modified Polystyrene Latex | 0.44 |
| Perfume | 1.11 |
| Sodium Chloride | 0.90 |

-continued

| Ingredient | wt. % |
| --- | --- |
| JAGUAR C-13-S | 0.0 or 0.70 |
| Sunscreen active (encapsulated or not) | 2 |
| Water | balance to 100 |

Some of the compositions prepared contained JAGUAR C-13-S, whilst others did not. The sunscreen active used was a mixture of Octocrylene (which is 2-ethylhexyl-2-cyano-3,3-diphenyl acrylate), Avobenzone (which is 4-4-butyl-4'-methoxydibenzoyl methane) and Benzophenone-3 (which is 2-hydroxy-4-methoxy benzophenone), in the ratio 7.6:6.1:6.1, and was provided either in encapsulated form or unencapsulated. If not encapsulated, the active was added to give 2 wt % of the total composition. If the sunscreen active was encapsulated, the capsules used supplied by SunSmart Inc as an emulsion which has a composition as follows:

| Ingredients | wt. % |
| --- | --- |
| Octocrylene | 7.6 |
| Avobenzone | 6.1 |
| Benzophenone-3 | 6.1 |
| Waxes | 32.6 |
| Water | 47.6 |

Thus the mixture of three sunscreen active makes up 37.8 wt % of the encapsulated sunscreen capsules non-aqueous contents, which constitute 52.4 wt % of the emulsion. The emulsion, when used, was added in sufficient quantity to provide the sunscreen active in an amount of 2 wt % of the total composition.

The amount of deposition of sunscreen active was measured as in example 1. The 9 measurements for each composition were averaged and the results obtained (including standard error of mean), are set out in the table below:

| Deposition Polymer present | Was sunscreen active encapsulated | Amount of sunscreen active deposited ($\mu$g/cm$^2$) |
| --- | --- | --- |
| * No | No | 4.32 ± 0.53 |
| * No | Yes | 5.06 ± 0.22 |
| * Yes | No | 8.12 ± 0.42 |
| Yes | Yes | 9.93 ± 0.44 |

* Comparative examples

As in Example 1, when the sunscreen active is encapsulated and deposition aid is present, the amount of sunscreen active deposited is greater than the amount deposited either when the sunscreen active is not encapsulated or when no polymer deposition aid is present.

What is claimed is:
1. A rinse-off liquid personal wash cleaning composition comprising:
 (a) 5 to 40% by wt. of said composition of a surfactant selected from the group consisting of anionic, nonionic, zwitterionic and cationic surfactants, soaps and mixtures thereof, wherein anionic surfactant comprises from about 4% by wt. of said composition;
 (b) a polymeric deposition aid comprising a polymer with a cationic charge; and

(c) sunscreen active trapped within a matrix defining a capsule, wherein the matrix is selected from natural waxes and synthetic modified waxes selected from the group consisting of alkyl wax esters, resins, and other vegetable components; clay treated microcrystalline waxes; oxidized hydrocarbon waxes; natural and synthetic beeswax, anti-oxidized beeswax, candelilia, carnauba, esterified natural plant derived fatty acids and alcohols; paraffin waxes; natural and synthetic oils; and mixtures thereof;

and wherein the amount of sunscreen in the capsule is from 5% to 60% by weight of the capsule.

2. A composition according to claim 1, wherein the amount of sunscreen capsules present in the composition is an amount such that the amount of sunscreen active in the composition is from 0.5% to 15% by weight.

3. A composition according to claim 2, wherein the amount of sunscreen capsules present in the composition is in an amount such that the amount of sunscreen active in the composition is from 1% to 12% by weight composition.

4. A composition according to claim 1 wherein the amount of sunscreen active in the sunscreen capsules provide from 5 to 40% by weight of those capsules.

5. A composition according to claim 4 wherein the amount of sunscreen active in the sunscreen capsules provide from 5 to 30% by weight of those capsules.

6. A composition according to claim 1 wherein the polymeric deposition aid is present in an amount from 0.1 to 3% by weight of the whole composition.

7. A composition according to claim 1, wherein said anionic surfactant comprises soap derived from materials having a $C_8$ to $C_{22}$ carbon chain wherein said chain is selected from group consisting of saturated chains, unsaturated chains and mixtures thereof.

* * * * *